United States Patent [19]

Glase et al.

[11] Patent Number: 5,270,312

[45] Date of Patent: Dec. 14, 1993

[54] SUBSTITUTED PIPERAZINES AS CENTRAL NERVOUS SYSTEM AGENTS

[75] Inventors: Shelly Glase, Ann Arbor; Juan C. Jaen, Plymouth; Sarah J. Smith; Lawrence D. Wise, both of Ann Arbor, all of Mich.

[73] Assignee: Warner-Lambert Company, Morris Plains, N.J.

[21] Appl. No.: 778,247

[22] Filed: Oct. 24, 1991

Related U.S. Application Data

[63] Continuation-in-part of Ser. No. 609,300, Nov. 5, 1990, abandoned.

[51] Int. Cl.$^5$ .................. A61K 31/495; A61K 31/50; C07D 403/02; C07D 401/02
[52] U.S. Cl. .................. 514/252; 514/253; 514/254; 514/255; 544/238; 544/295; 544/296; 544/360; 544/362; 544/363; 544/367; 544/370; 544/373; 544/376; 544/379
[58] Field of Search .............. 514/255, 252, 253, 254; 544/296, 360, 364, 295, 363, 238, 342, 367, 370, 373, 376, 379

[56] References Cited

U.S. PATENT DOCUMENTS

| | | | |
|---|---|---|---|
| 3,458,514 | 7/1969 | Palazzo | 544/392 |
| 3,856,790 | 12/1974 | Freed et al. | 544/141 |
| 4,831,031 | 5/1989 | Lowe, III et al. | 514/254 |
| 4,883,795 | 11/1989 | Lowe, III et al. | 514/253 |
| 4,891,375 | 1/1990 | Lowe, III | 514/252 |

Primary Examiner—Mukund J. Shah
Assistant Examiner—Matthew V. Grumbling
Attorney, Agent, or Firm—Francis J. Tinney

[57] ABSTRACT

Substituted piperazines and derivatives of Formula I

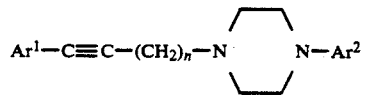

are described, as well as methods for the preparation and pharmaceutical composition of the same, which are useful as central nervous system agents and are particularly useful as dopaminergic, antipsychotic, and antihypertensive agents as well as for treating hyperprolactinaemia-related conditions and central nervous system disorders.

5 Claims, No Drawings

SUBSTITUTED PIPERAZINES AS CENTRAL NERVOUS SYSTEM AGENTS

This is a continuation-in-part of U.S. application Ser. No. 07/609,300 filed Nov. 5, 1990, now abandoned.

BACKGROUND OF THE INVENTION

The present invention relates to novel substituted piperazines and derivatives thereof useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents.

EP 0 211 457 A2 discloses compounds of formula:

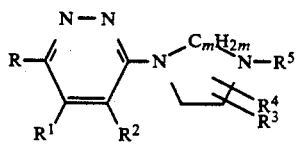

wherein R is hydrogen, halo, $C_{1-6}$-alkyloxy, hydroxy or phenyl; m is 2 or 3; $R^1$, $R^2$, $R^3$, $R^4$ are each independently hydrogen or $C_{1-6}$-alkyl or where $R^3$ and $R^4$ are substituted on a different carbon atom, $R^3$ and $R^4$ taken together may form a bivalent radical —$CH_2$—$CH_2$—; $R^5$ is (aryl)$C_{2-6}$-alkenyl, (aryl)$C_{2-6}$-alkynyl, (aryl)(hydroxy)$C_{1-6}$-alkyl or (aryl)(oxo)$C_{1-6}$-alkyl; the n-oxide forms; and pharmaceutically acceptable acid addition salts and the possible stereochemically isomeric forms thereof having antitussive/analgesic properties.

GB 1055548 discloses compounds of formula

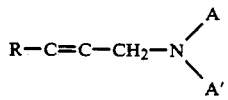

wherein R represents unsubstituted phenyl or phenyl substituted by methyl, halogen, nitro, amino, (lower alkanoyl)amino, or lower alkoxyl; and either A is alkyl of 1 to 4 carbon atoms and A' is alkyl of 1 to 4 carbon atoms, benzyl, chlorobenzyl, or dimethoxybenzyl; or A and A', together with the adjacent nitrogen atom, form one of the following heterocyclic rings: pyrrolidino, morpholino, thiomorpholino, 4-phenylpiperidino, 4-phenyl-4-hydroxypiperidino, N'-methylpiperazino, N'-benzylpiperazino, N'-phenylpiperazino, N'-chlorophenylpiperazino, N'-tolylpiperazino, N'-methoxyphenylpiperazino, N'-(β-hydroxyethyl)piperazino, N'-(β-acetoxyethyl)piperazino, N'-(β-propionyloxyethyl)piperazino, N'-carbethoxypiperazino, hexamethyleneimino, and heptamethyleneimino; provided that when R is phenyl, p-methoxyphenyl, o- or p-nitrophenyl, or o-aminophenyl,

does not represent dimethylamino or diethylamino; and their acid addition salts, especially those containing physiologically innocuous anions having antiulcer activity.

The aforementioned references do not teach nor suggest the combination of structural variations of the compounds of the present invention nor their use as dopaminergic agents described hereinafter.

SUMMARY OF THE INVENTION

Accordingly, the present invention provides a compound of Formula I

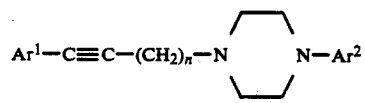

wherein
n is an integer of 2, 3, or 4;
$Ar^1$ and $Ar^2$ are each independently
  aryl,
  aryl substituted by one to four substituents selected from the group consisting of
    halogen,
    lower alkyl,
    lower alkoxy,
    lower thioalkoxy,
    hydroxy,
    lower acyloxy,
    amino,
    lower alkyl amino,
    nitro,

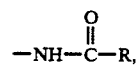

wherein R is
    aryl,
    lower alkyl,
    trifluoromethyl or a 5- or 6-membered heteroaromatic ring comprising one or more heteroatoms selected from N, S, and O,
  —NH—$SO_2$R, wherein R is as defined above or
  —N—($SO_2$R)$_2$, wherein R is as defined above,
  a 5- or 6-membered heteroaromatic ring comprising one or more heteroatoms selected from N, S, and O,
  a 5- or 6-membered heteroaromatic ring comprising one or more heteroatoms selected from N, S, and O, substituted by
    halogen,
    lower alkyl,
    lower alkoxy,
    hydroxy,
    lower acyloxy,
    amino,
    lower alkyl amino,
    nitro,

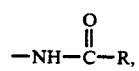

'wherein R is as defined above,
—NH—$SO_2$R, wherein R is as defined above, or
—N—($SO_2$R)$_2$, wherein R is as defined above, a 8-, 9-, or 10-membered heteroaromatic bicyclic ring comprising one or more heteroatoms selected from N, S, and O, or a 8-, 9-, or 10-membered heteroaromatic bicyclic ring comprising one or more heteroatoms selected from N, S, and O, substituted by
halogen,
lower alkyl,
lower alkoxy,
hydroxy,
lower acyloxy,
amino
lower alkyl amino,
nitro,

wherein R is as defined above,
—NH—SO$_2$R, wherein R is as defined above, or
—N—(SO$_2$R)$_2$, wherein R is as defined above;
or a pharmaceutically acceptable acid addition salt thereof, with the exclusion of a compound of Formula I wherein Ar$^2$ is 3-pyridazinyl.

As dopaminergic agents, the compounds of Formula I are useful as antipsychotic agents for treating psychoses such as schizophrenia. They are also useful as antihypertensives and for the treatment of disorders which respond to dopaminergic activation. Thus, other embodiments of the present invention include the treatment, by a compound of Formula I, of hyperprolactinaemia-related conditions, such as galactorrhea, amenorrhea, menstrual disorders and sexual dysfunction, and several central nervous system disorders such as Parkinson's disease, Huntington's chorea, and depression.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group or phenyl group substituted by one to four substituents selected from halogen, lower alkyl, lower alkoxy, lower thioalkoxy, hydroxy, lower acyloxy, amino, lower alkyl amino, nitro,

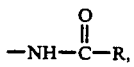

wherein R is aryl, lower alkyl, trifluoromethyl or a 5- or 6-membered heteroaromatic ring as defined hereinafter, —NH—SO$_2$R, wherein R is lower alkyl trifluoromethyl or a 5- or 6-membered heteroaromatic ring as defined hereinafter, or —N—(SO$_2$R)$_2$, wherein R is lower alkyl, trifluoromethyl, or a 5- or 6-membered heteroaromatic ring as defined hereinafter.

The term "5- or 6-membered heteroaromatic ring" comprises but is not limited to: 2-, 3-, or 4-pyridinyl, 2-, 4-, or 5-pyrimidinyl, 2-pyrazinyl, 2- or 3 furanyl, 2- or 3-thienyl, 2-, 4-, or 5-imidazolyl, 2-, 4-, or 5-thiazolyl, unsubstituted or substituted by halogen, lower alkyl, hydroxy, lower acyloxy lower alkoxy, amino, lower alkyl amino, nitro,

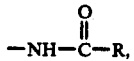

R is aryl, lower alkyl, trifluoromethyl or a 5- or 6-membered heteroaromatic ring as defined herein for "5- or 6-membered heteroaromatic ring", —NH—SO$_2$R, wherein R is lower alkyl, trifluoromethyl, or a 5- or 6-membered heteroaromatic ring as defined herein for "5- or 6-membered heteroaromatic ring", or —N—(SO$_2$R)$_2$, wherein R is lower alkyl, trifluoromethyl, or a 5- or 6-membered heteroaromatic ring as defined herein for "5- or 6-membered heteroaromatic ring".

The term "8 , 9-, or 10-membered heteroaromatic bicyclic ring" comprises but is not limited to: 2-, 3-, 4-, 5-, 6-, or 7-indolyl, 2-, 3-, 4-, 5-, 6-, or 7-benzo[b]thienyl, 2-, 3-, 4-, 5-, 6-, 7-, or 8-quinolinyl, 1-, 3-, 4-, 5 , 6-, 7-, or 8-isoquinolinyl, 2-, 3-, 4-, 5-, 6-, or 7-(1,8)naphthyridinyl, unsubstituted or substituted by halogen, lower alkyl, hydroxy, lower acyloxy, lower alkoxy, amino, lower alkyl amino, nitro,

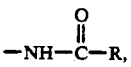

wherein R is aryl, lower alkyl, trifluoromethyl 5- or 6-membered heteroaromatic ring as defined herein for "5- or 6-membered heteroaromatic ring", —NH—SO$_2$R, wherein R is lower alkyl, trifluoromethyl, or a 5- or 6-membered heteroaromatic ring as defined herein for "5- or 6-membered heteroaromatic ring", or —N—(SO$_2$R)$_2$, wherein R is lower alkyl, trifluoromethyl, or a 5- or 6-membered heteroaromatic ring as defined herein for "5- or 6-membered heteroaromatic ring".

"Lower alkoxy" and "thioalkoxy" are O-alkyl or S-alkyl of from one to six carbon atoms as defined above for "lower alkyl."

"Lower acyloxy" is

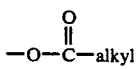

of from one to six carbon atoms as defined above for "lower alkyl".

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

"Noble metal" is platinum, palladium, rhodium, ruthenium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogen phosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the equivalent to unsolvated forms and are intended to be encompassed within the scope of the present invention.

A preferred compound of Formula I is one in which $Ar^1$ and $Ar^2$ are each independently
  aryl,
  aryl substituted by one to four substituents selected from the group consisting of
    halogen,
    lower alkyl,
    lower alkoxy,
    lower thioalkoxy,
    hydroxy,
    lower acyloxy,
    amino,
    lower alkyl amino
    nitro, or

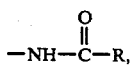

wherein R is
      aryl,
      lower alkyl,
      trifluoromethyl,
      2-, 3-, or 4-pyridinyl,
      2-, 4-, or 5-pyrimidinyl,
      2-pyrazinyl,
      2- or 3-furanyl,
      2- or 3-thienyl,
      2-, 4-, or 5-imidazolyl, or
      2-, 4-, or 5-thiazolyl,
  2-, 3-, or 4-pyridinyl,
  2-, 3-, or 4-pyridinyl substituted by
    halogen,
    lower alkyl,
    lower alkoxy,
    hydroxy,
    lower acyloxy,
    amino,
    lower alkyl amino,
    nitro,

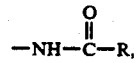

wherein R is as defined above,
    —NH—SO$_2$R, wherein R is as defined above, or
    —N—(SO$_2$R)$_2$, wherein R is as defined above,
  2-, 4-, or 5-pyrimidinyl,
  2-, 4-, or 5-pyrimidinyl substituted by
    halogen,
    lower alkyl,
    lower alkoxy,
    hydroxy,
    lower acyloxy,
    amino,
    lower alkyl amino,
    nitro,

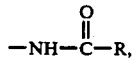

wherein R is as defined above,
    —NH—SO$_2$R, wherein R is as defined above, or
    —N—(SO$_2$R)$_2$, wherein R is as defined above,
  2-pyrazinyl,
  2-pyrazinyl substituted by
    halogen
    lower alkyl,
    lower alkoxy,
    hydroxy,
    lower acyloxy,
    amino,
    lower alkyl amino,
    nitro,

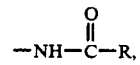

wherein R is as defined above,
    —NH—SO$_2$R, wherein R is as defined above, or
    —N—(SO$_2$R)$_2$, wherein R is as defined above,
  2- or 3-furanyl,
  2- or 3-furanyl substituted by
    halogen,
    lower alkyl,
    lower alkoxy,
    hydroxy,
    lower acyloxy,
    amino,
    lower alkyl amino,
    nitro,

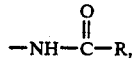

wherein R is as defined above,
    —NH—SO$_2$R, wherein R is as defined above, or
    —N—(SO$_2$R)$_2$ wherein R is as defined above, 2- or 3-thienyl,
2- or 3-thienyl substituted by
  halogen,
  lower alkyl,
  lower alkoxy,
  hydroxy,
  lower acyloxy,
  amino,
  lower alkyl amino,
  nitro,

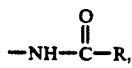

wherein R is as defined above,
  —NH—SO₂R wherein R is as defined above, or
  —N—(SO₂R)₂, wherein R is as defined above,
2-, 4-, or 5-imidazolyl,
2-, 4-, or 5-imidazolyl substituted by
  halogen,
  lower alkyl,
  lower alkoxy,
  hydroxy,
  lower acyloxy,
  amino,
  lower alkyl amino,
  nitro,

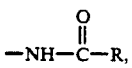

wherein R is as defined above,
  —NH—SO₂R, wherein R is as defined above, or
  —N—(SO₂R)₂, wherein R is as defined above,
2-, 4-, or 5-thiazolyl,
2-, 4-, or 5-thiazolyl substituted by
  halogen,
  lower alkyl,
  lower alkoxy,
  hydroxy,
  lower acyloxy,
  amino,
  lower alkyl amino,
  nitro,

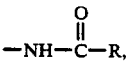

wherein R is as defined above,
  —NH—SO₂R wherein R is as defined above, or
  —N—(SO₂R)₂ wherein R is as defined above,
2-, 3-, 4-, 5-, 6-, or 7-indolyl,
2-, 3-, 4-, 5-, 6-, or 7-indolyl substituted by
  halogen,
  lower alkyl,
  lower alkoxy,
  hydroxy,
  lower acyloxy,
  amino,
  lower alkyl amino,
  nitro,

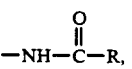

wherein R is as defined above,
  —NH—SO₂R, wherein R is as defined above, or
  —N—(SO₂R)₂, wherein R is as defined above,
2-, 3-, 4-, 5-, 6-, or 7-benzo[b]thienyl,
2-, 3-, 4-, 5-, 6-, or 7-benzo[b]thienyl substituted by
  halogen,
  lower alkyl,
  lower alkoxy,
  hydroxy,
  lower acyloxy,
  amino,
  lower alkyl amino,
  nitro,

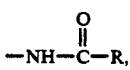

wherein R is as defined above,
  —NH—SO₂R, wherein R is as defined above, or
  —N—(SO₂R)₂, wherein R is as defined above,
2-, 3-, 4-, 5-, 6-, 7-, or 8-quinolinyl,
2-, 3-, 4-, 5 , 6-, 7-, or 8-quinolinyl substituted by
  halogen,
  lower alkyl,
  lower alkoxy,
  hydroxy,
  lower acyloxy,
  amino,
  lower alkyl amino,
  nitro,

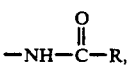

wherein R is as defined above,
  —NH—SO₂R, wherein R is as defined above, or
  —N—(SO₂R)₂, wherein R is as defined above,
1-, 3-, 4-, 5 , 6-, 7-, or 8-isoquinolinyl,
1-, 3-, 4-, 5-, 6-, 7-, or 8-isoquinolinyl substituted by
  halogen,
  lower alkyl,
  lower alkoxy,
  hydroxy,
  lower acyloxy,
  amino,
  lower alkyl amino,
  nitro,

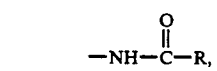

wherein R is as defined above,
  —NH—SO₂R, wherein R is as defined above, or
  —N—(SO₂R)₂, wherein R is as defined above,
2-, 3-, 4-, 5 , 6-, or 7-(1,8)naphthyridinyl, or
2-, 3-, 4-, 5 , 6-, or 7-(1,8)naphthyridinyl substituted by
  halogen,
  lower alkyl,
  lower alkoxy,
  hydroxy,
  lower acyloxy,
  amino,
  lower alkyl amino,
  nitro,

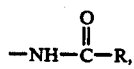

wherein R is as defined above,
—NH—SO₂R, wherein R is as defined above, or
—N—(SO₂R)₂ wherein R is as defined above.

Another preferred compound of Formula I is one in which
n is 2 or 3 and
Ar¹ and Ar² are each independently
   aryl,
   aryl substituted by one to four substituents selected from the group consisting of
      halogen,
      lower alkyl,
      lower alkoxy,
      lower thioalkoxy,
      hydroxy,
      lower acyloxy,
      amino,
      lower alkyl amino,
      nitro, or

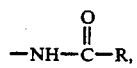

wherein R is
      aryl,
      lower alkyl,
      trifluoromethyl,
      2-, 3-, or 4 pyridinyl,
      2-, 4-, or 5 pyrimidinyl,
      2-pyrazinyl,
      2- or 3-furanyl,
      2- or 3-thienyl,
      2-, 4-, or 5-imidazolyl, or
      2-, 4-, or 5-thiazolyl,
2-, 3-, or 4-pyridinyl,
2-, 3-, or 4-pyridinyl substituted by
   halogen,
   lower alkyl,
   lower alkoxy,
   hydroxy,
   lower acyloxy,
   amino,
   lower alkyl amino,
   nitro,

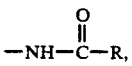

wherein R is as defined above,
   —NH—SO₂—R, wherein R is as defined above, or
   —N—(SO₂R)₂, wherein R is as defined above,
2-, 4-, or 5-pyrimidinyl,
2-, 4-, or 5-pyrimidinyl substituted by
   halogen,
   lower alkyl,
   lower alkoxy,
   hydroxy,
   lower acyloxy,
   amino,
   lower alkyl amino,
   nitro,

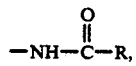

wherein R is as defined above,
   —NH—SO₂—R, wherein R is as defined above, or
   —N—(SO₂R)₂, wherein R is as defined above,
2- or 3-thienyl,
2- or 3-thienyl substituted by
   halogen,
   lower alkyl,
   lower alkoxy,
   hydroxy,
   lower acyloxy,
   amino,
   lower alkyl amino,
   nitro,

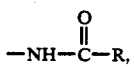

where R is as defined above,
   —NH—SO₂—R, wherein R is as defined above, or
   —N—(SO₂R)₂, wherein R is as defined above,
4- or 5 thiazolyl,
4- or 5-thiazolyl substituted by
   halogen,
   lower alkyl,
   lower alkoxy,
   hydroxy,
   lower acyloxy,
   amino,
   lower alkyl amino,
   nitro,

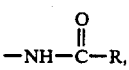

wherein R is as defined above,
   —NH—SO₂—R, wherein R is as defined above, or
   —N—(SO₂R)₂, wherein R is as defined above,
2- or 3-indolyl,
2- or 3-indolyl substituted by
   halogen,
   lower alkyl,
   lower alkoxy,
   hydroxy,
   lower acyloxy,
   amino,
   lower alkyl amino,
   nitro,

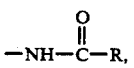

wherein R is as defined above,
   —NH—SO₂—R, wherein R is as defined above, or
   —N—(SO₂R)₂, wherein R is as defined above,
2-, 3-, or 4-quinolinyl,
2-, 3-, or 4-quinolinyl substituted by
   halogen,
   lower alkyl,
   lower alkoxy,
   hydroxy,
   lower acyloxy, amino,
lower alkyl amino,
nitro,

wherein R is as defined above,
—NH—SO$_2$—R, wherein R is as defined above, or
—N—(SO$_2$R)$_2$, wherein R is as defined above
1-, 3-, -- 4-isoquinolinyl, or
1-, 3-, or 4-isoquinolinyl substituted by
halogen,
lower alkyl,
lower alkoxy,
hydroxy,
lower acyloxy,
amino,
lower alkyl amino,
nitro,

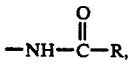

wherein R is as defined above,
—NH—SO$_2$—R, wherein R is as defined above, or
—NH—(SO$_2$R)$_2$, wherein R is as defined above.
Particularly preferred compounds are:
3[4-[4-(2-Pyridinyl)-1-piperazinyl]-1-butynyl]quinoline;
1-(4-Fluorophenyl)-4-[4-(3-pyridinyl)-3-butynyl]piperazine;
1(2-Pyridinyl)-4-[4-(3-pyridinyl)-3-butynyl]piperazine;
2-[4-[4-(3-Pyridinyl)-3-butynyl]-1-piperazinyl]-pyrimidine;
1-[4-(5-Nitro-2-pyridinyl)-3-butynyl]4-(2-pyridinyl)piperazine;
1-[4-(4-Nitrophenyl) 3-butynyl]-4-(2-pyridinyl)piperazine;
6-[4-(2-Pyridinyl)-1-piperazinyl]-1-butynyl]-3-pyridinamine;
4-[4-[4-(2-Pyridinyl)-1-piperazinyl]-1-butynyl]benzenamine;
5-[4-[4-(2-Pyridinyl)-1-piperazinyl]-1-butynyl]-2-thiazolamine;
5-[4-[4-(2-Pyridinyl)-1-piperazinyl]-1-butynyl]-2pyridinamine; and
3-[4-(2-Pyridinyl)-1-piperazinyl]-1-butynyl]1H-indole;
or a pharmaceutically acceptable acid addition salt thereof.

The compounds of Formula I are valuable dopaminergic agents. The tests employed indicate that compounds of Formula I possess dopaminergic activity. Thus, the compounds of Formula I were tested for their ability to inhibit locomotor activity in mice according to the assay described by J. R. McLean, et al, *Pharmacology, Biochemistry and Behavior*, Volume 8, pages 97–99 (1978); for their ability to inhibit [$^3$H]-spiroperidol binding in a receptor assay described by D. Grigoriadis and P. Seeman, *Journal of Neurochemistry*, Volume 44, pages 1925–1935 (1985); and for their ability to inhibit dopamine synthesis in rats according to the protocol described by J. R. Walters and R. H. Roth, *Naunyn-Schmiedeberg's Archives of Pharmacology*, Volume 296, pages 5–14 (1976). The above test methods are incorporated herein by reference. The data in the table show the dopaminergic activity of representative compounds of Formula 1.

| Biological Activity of Compounds of Formula I | | | | |
|---|---|---|---|---|
| Example Number | Compound | Inhibition of Locomotor Activity in Mice ED$_{50}$, mg/kg, IP | % Reversal of Brain Dopamine Synthesis in Rats at 10 mg/kg, IP | Inhibition of [$^3$H]Spiroperidol Binding IC$_{50}$, nM |
| 1 | 3-[4-[4-(2-Pyridinyl)-1-piperazinyl]-1-butynyl]quinoline | 1.5 | | 177 |
| 2 | 1-(4-Fluorophenyl)-4-[4-(3-pyridinyl)-3-butynyl]piperazine | 4.7 | 20 | 2,326 |
| 3 | 1-(2-Pyridinyl)-4-[4-(3-pyridinyl)-3-butynyl]-piperazine | 2.2 | | 6,530 |
| 5 | 1-[4-(5-Nitro-2-pyridinyl)-3-butynyl]-4-(2-pyridinyl)piperazine; | 14.1 | | >10,000 |
| 6 | 1-[4-(4-Nitrophenyl)-3-butynyl]-4-(2-pyridinyl)-piperazine; | 7.7 | | 2500 |
| 7 | 6-[4-[4-(2-Pyridinyl)-1-piperazinyl]-1-butynyl]-3-pyridinamine; | 0.35 | 24 | 1900 |
| 8 | 4-[4-[4-(2-Pyridinyl)-1-piperazinyl]-1-butynyl]-benzenamine; | 0.56 | 63 | 611 |

Also, the present invention provides a process for the preparation of a compound of Formula I:

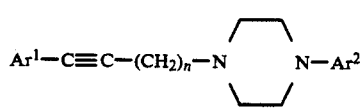

wherein
n is an integer of 2, 3, or 4;
Ar$^1$ and Ar$^2$ are each independently
aryl,
aryl substituted by one to four substituents selected from the group consisting of
halogen, lower alkyl,
lower alkoxy,
lower thioalkoxy,
hydroxy,
lower acyloxy,
amino,
lower alkyl amino,
nitro,

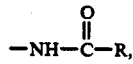
—NH—C—R, wherein R is
aryl,
lower alkyl,
trifluoromethyl or a 5- or 6-membered heteroaromatic ring comprising one or more heteroatoms selected from N, S, and O,
—NH—SO$_2$R, wherein R is as defined above or
—N—(SO$_2$R)$_2$, wherein R is as defined above,
a 5- or 6-membered heteroaromatic ring comprising one or more heteroatoms selected from N, S, and O,
a 5- or 6-membered heteroaromatic ring comprising one or more heteroatoms selected from N, S, and O, substituted by
halogen,
lower alkyl,
lower alkoxy,
hydroxy,
lower acyloxy,
amino,
lower alkyl amino,
nitro,

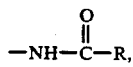
—NH—C—R, wherein R is as defined above,
—NH—SO$_2$R, wherein R is as defined above, or
—N—(SO$_2$R)$_2$, wherein R is as defined above,
a 8-, 9-, or 10-membered heteroaromatic bicyclic ring comprising one or more heteroatoms selected from N, S, and O, or
a 8-, 9-, or 10-membered heteroaromatic bicyclic ring comprising one or more heteroatoms selected from N, S, and O, substituted by
halogen,
lower alkyl,
lower alkoxy,
hydroxy,
lower acyloxy,
amino
lower alkyl amino,
nitro,

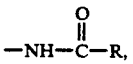
—NH—C—R, wherein R is as defined above,
—NH—SO$_2$R, wherein R is as defined above, or
—N—(SO$_2$R)$_2$, wherein R is as defined above;
or a pharmaceutically acceptable acid addition salt thereof, with the exclusion of a compound of Formula I wherein Ar$^2$ is 3-pyridazinyl, which comprises:
a) reacting a compound of Formula II

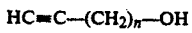
Ar$^1$—X     II wherein X is Cl, Br, or I, and Ar$^1$ is as defined above with a compound of Formula III HC≡C—(CH$_2$)$_n$—OH     III wherein n is an integer of 2, 3, or 4 in a solvent, such as, for example, dichloromethane and the like, in the presence of an acid scavenger such as, for example, triethylamine and the like, and in the presence of a catalytically effective amount of bis(triarylphosphine)palladium(II)chloride ([(Ar$^3$)$_3$P]$_2$PdCl$_2$), bis(triarylphosphine)palladium(II) acetate([(Ar$^3$)$_3$P]$_2$Pd(O$_2$CCH$_3$)$_2$), or triarylphosphinepalladium(II)acetate (Ar$^3$)$_3$P/Pd(O$_2$CCH$_3$)$_2$), wherein Ar$^3$ is phenyl or phenyl substituted by lower alkyl and cuprous iodide (CuI) to afford a compound of Formula IV Ar$^1$—C≡C—(CH$_2$)$_n$—OH     IV wherein Ar$^1$ and n are as defined above. Preferably, the reaction is carried out in a solvent such as, for example, dichloromethane and the like in the presence of triethylamine and bis(triphenylphosphine)palladium(II)chloride and cuprous iodide;

b) reacting an alcohol of Formula IV with an alkyl- or aryl sulfonyl halide such as, for example, methanesulfonyl chloride and the like, in a solvent such as, for example, dichloromethane and the like, and in the presence of an acid scavenger such as, for example, triethylamine, diisopropylethylamine and the like, to afford a compound of Formula Va:

Ar$^1$—C≡C—(CH$_2$)$_n$—L$_a$     Va wherein L$_a$ is alkyl- or aryl-sulfonyloxy and Ar$^1$ and n are as defined above. Preferably, the reaction is carried out with methanesulfonyl chloride in dichloromethane in the presence of triethylamine or alternatively, reacting an alcohol of Formula IV with a triarylphosphine such as, for example, triphenylphosphine and the like, combined with a tetrahalomethane such as, for example, tetrabromomethane and the like, to afford a compound of Formula Vb Ar$^1$—C≡C—(CH$_2$)$_n$—L$_b$     Vb wherein L$_b$ is a halogen atom and Ar$^1$ and n are as defined above. Preferably, the reaction is carried out with triphenylphosphine and tetrabromomethane;

c) reacting a compound of Formula Va or Vb with a compound of Formula VI

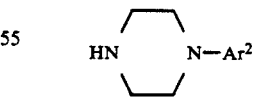
     VI wherein Ar$^2$ is as defined above, in a solvent such as, for example, dimethylformamide and the like, in the presence of a base such as, for example, sodium bicarbonate and the like, to afford a compound of Formula I above. Preferably the reaction is carried out in dimethylformamide in the presence of sodium bicarbonate.

The present invention provides another process for the preparation of a compound of Formula I above, which comprises:
a) reacting a compound of Formula II Ar¹—X    II wherein X is Cl, Br or I and Ar¹ is as defined above, with the compound of Formula VII HC≡C—SiMe₃    VII in a solvent such as, for example, dichloromethane and the like, in the presence of an acid scavenger such as, for example, triethylamine and the like, and in the presence of a catalytically effective amount of bis(triarylphosphine)palladium(II)chloride ([(Ar³)₃P]₂PdCl₂), bis(triarylphosphine)palladium(II) acetate([(Ar³)₃P]₂ Pd(O₂CCH₃)₂), or triarylphosphinepalladium(II)acetate ((Ar³)₃P/Pd(O₂CCH₃)₂), wherein Ar₃ is phenyl or phenyl substituted by lower alkyl and cuprous iodide (CuI) to afford a compound of Formula VIII Ar¹—C≡C—SiMe₃    VIII wherein Ar¹ is as defined above. Preferably, the reaction is carried out in a solvent such as, for example, dichloromethane and the like in the presence of triethylamine and bis(triphenylphosphine)palladiumII)chloride and cuprous iodide;

b) removing the trimethylsilyl group using a base such as, for example, potassium hydroxide and the like, and an alcohol such as, for example, ethanol and the like, to afford a compound of Formula IX Ar¹—CH≡CH    IX wherein Ar¹ is as defined above. Preferably, the reaction is carried out in ethanol in the presence of potassium hydroxide;

c) reacting a compound of Formula IX with an organolithium compound such as, for example, n-butyllithium and the like, at a temperature of about 0° C., and with a compound of Formula X

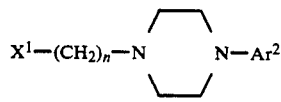    X wherein X¹ is Cl, Br, or I and n and Ar² are as defined above in a solvent such as, for example, a mixture of tetrahydrofuran:hexamethylphosphoric triamide and the like, to afford a compound of Formula I. Preferably, the reaction is carried out with n-butyllithium in a mixture of tetrahydrofuranhexamethylphosphoric triamide.

Preferably a compound of Formula Ia

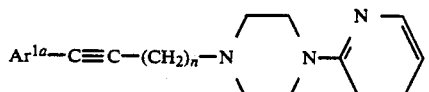    Ia wherein n is an integer of 2, 3, or 4 and Ar¹ᵃ is
aryl substituted by nitro, or
2-, 3-, or 4-pyridinyl substituted by nitro or a pharmaceutically acceptable acid addition salt thereof, comprises reacting a compound of Formula IIa Ar¹ᵃ—X    IIa wherein Ar¹ᵃ and X are as defined above with a compound of Formula XII

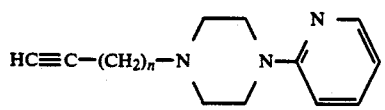    XII wherein n is as defined above using the methodology used to prepare a compound of Formula IV from a compound of Formula II and a compound of Formula III to afford a compound of Formula Ia.

Preferably, a compound of Formula Ib

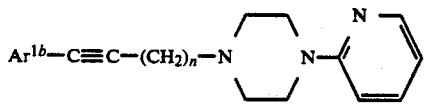    Ib wherein n is an integer of 2, 3, or 4 and Ar¹ᵇ is
aryl substituted by amino, or
2-, 3-, or 4-pyridinyl substituted by amino or a pharmaceutically acceptable acid addition salt thereof, comprises reacting a compound of Formula Ia with hydrogen in the presence of a catalyst such as, for example, platinum, palladium, rhodium, ruthenium, and the like, iron in the presence of an acid such as, for example, hydrochloric acid and the like in a solvent such as, for example, ethanol and the like at about 0° C. to about the reflux temperature of the solvent to afford a compound of Formula Ib. Preferably, the reaction is carried out with iron and hydrochloric acid in ethanol at about 80° C.

Preferably, a compound of Formula Ic

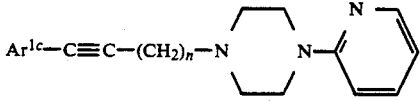    Ic wherein n is an integer of 2, 3, or 4 and Ar¹ᶜ is
aryl substituted by

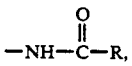
—NH—C—R, wherein R is
aryl,
lower alkyl,
trifluoromethyl, or
a 5- or 6-membered heteroaromatic ring comprising one or more heteroatoms selected from N, S, and O,
—NH—SO₂R, wherein R is as defined above, or
—N—(SO₂R)₂, wherein R is as defined above, or
2-, 3-, or 4-pyridinyl substituted by

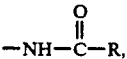
—NH—C—R, wherein R is as defined above,
—NH—SO₂R, wherein R is as defined above, or
—N—(SO₂R)₂, wherein R is as defined above, or a pharmaceutically acceptable acid addition salt thereof, comprises reacting a compound of Formula Ib with a compound of Formula XIII $$R^1—X \qquad\qquad XIII$$

wherein $R_1$ is $$R-\underset{\underset{O}{\|}}{C}-$$

or $(R—SO_2)_2$—and X is as defined above in the presence of a base such as, for example, triethylamine and the like and optionally a catalytic quantity of N,N-dimethylaminopyridine in a solvent such as, for example, dichloromethane and the like at about 0° C. to about the reflux temperature of the solvent to afford a compound of Formula Ic. Preferably, the reaction is carried out in the presence of triethylamine in dichloromethane containing a catalytic amount of N,N-dimethylaminopyridine at about room temperature. In the case wherein the substituent group in $Ar^{1c}$ in a compound of Formula Ic is $R—SO_2NH—$ it is prepared by reacting a compound of Formula Ib with a compound of Formula XIV $$(R—SO_2)_2O \qquad\qquad XIV$$

wherein R is as defined above in the presence of a base such as, for example, triethylamine and the like in a solvent such as, for example, dichloromethane and the like at about −78° C. to afford a compound of Formula Ic. Preferably, the reaction is carried out in the presence of triethylamine in dichloromethane at about −78° C.

Preferably, a compound of Formula Id $$Ar^{1d}—C\equiv C—(CH_2)_n—N\underset{\diagdown\underline{\quad}\diagup}{\overset{\diagup\overline{\quad}\diagdown}{\phantom{X}}}N\underset{\diagdown\underline{\quad}\diagup}{\overset{\diagup N\diagdown}{\phantom{X}}} \qquad\qquad Id$$

wherein n is an integer of 2, 3, or 4 and $Ar^{1d}$ is aryl substituted by lower alkyl amino or 2-, 3-, or 4-pyridinyl substituted by lower alkyl amino or a pharmaceutically acceptable acid addition salt thereof, comprises reacting a compound of Formula Ib with a compound of Formula XV $$R_2—\underset{\underset{O}{\|}}{C}H \qquad\qquad XV$$

wherein $R^2$ is lower alkyl in the presence of a metal hydride such as, for example, sodium cyanoborohydride, sodium triacetoxyborohydride, lithium aluminum hydride and the like optionally in the presence of an acid such as, for example, acetic acid and the like in a solvent such as, for example, dichloroethane, dichloromethane and the like at about 0° C. to about room temperature to afford a compound of Formula Id. Preferably, the reaction is carried out with sodium triacetoxyborohydride in the presence of acetic acid in dichloroethane at about room temperature. Alternatively, in the case wherein the substituent group in $Ar^{1d}$ in a compound of Formula Id is methylamino it is prepared by reacting a compound of Formula Ib with a mixture of acetic anhydride and formic acid in a solvent such as, for example, tetrahydrofuran and the like and subsequent reaction with a metal hydride reagent such as, for example, lithium aluminum hydride and the like to afford a compound of Formula Id.

A compound of Formula X is prepared from a compound of Formula VI and a compound of Formula XI $$X^1—(CH_2)_n—X^1 \qquad\qquad XI$$

wherein $X^1$ and n are as defined above in the presence of a solvent such as, for example, dichloromethane and the like, in the presence of an acid scavenger such as, for example, triethylamine and the like, to afford a compound of Formula X. Preferably, the reaction is carried out in dichloromethane in the presence of triethylamine.

A compound of Formula XII is prepared from a compound of Formula XVI $$HC\equiv C—(CH_2)_n—L \qquad\qquad XVI$$

wherein L is a halogen atom or an alkyl or arylsulfonyloxy and n is as defined above with the compound of Formula XVII $$HN\underset{\diagdown\underline{\quad}\diagup}{\overset{\diagup\overline{\quad}\diagdown}{\phantom{X}}}N\underset{\diagdown\underline{\quad}\diagup}{\overset{\diagup N\diagdown}{\phantom{X}}} \qquad\qquad XVII$$

using the methodology used to prepare a compound of Formula I from a compound of Formula Va or Vb and VI.

A compound of Formula XVI is prepared from a compound of Formula III using the methodology used to prepare a compound of Formula Va and Vb from a compound of Formula IV.

Compounds of Formula II, IIa, III, VI, VII, XI, XIII, XIV, XV, and XVII are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxynethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferable in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg, according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred compounds of the invention and methods for their preparation.

EXAMPLE 1

3-[4-[4-(2-Pyridinyl)-1-piperazinyl]-1-butynyl]-quinoline

Step (a): Preparation of 4-(3-Quinolinyl)-3-butyn-1-ol

A solution of 3-bromoquinoline (13.57 mL, 0.10 mol) and 3-butyn-1-ol (9.0 mL, 0.12 mol) in 40 mL of triethylamine and 75 mL of dichloromethane is degassed by bubbling in dry nitrogen for 15 minutes, and 0.7 g (0.001 mol) of bis(triphenylphosphine)palladium chloride and 0.013 g of cuprous iodide are added. The flask is flushed with nitrogen and the mixture is heated to reflux for 5 hours. The cooled mixture is diluted with dichloromethane and washed with water, dried (sodium sulfate), and concentrated to give 27 g of an oil. The oil is triturated with diethyl ether to give 18.2 g of the title compound as a tan solid; mp 95.7°-96.7° C.

Step (b): Preparation of 3-[4-[4-(2-Pyridinyl)-1-piperazinyl]-1-butynyl]quinoline A solution of the alcohol prepared in Step (a) (1.98 g, 0.01 mol), N,N-diisopropylethylamine (3.5 mL, 0.02 mol) and a catalytic amount of 4-dimethylaminopyridine in 100 mL of dichloromethane is cooled to 0° C., and methanesulfonyl chloride (0.8 mL, 0.0105 mol) is added dropwise. The solution is stirred at 0° C. for 18 hours, and then concentrated under reduced pressure. The residue is taken up in dimethylformamide (20 mL), and to this solution is added 1-(2-pyridinyl)piperazine (2.45 g, 0.015 mol) and sodium bicarbonate (3.4 g, 0.04 mol). The mixture is heated at 40° C. for 5 hours and the solvent is removed under reduced pressure. The residue is partitioned between 50 mL of ethyl acetate and 50 mL of water. The aqueous layer is extracted with 50 mL of ethyl acetate and the combined organic layers are dried (sodium sulfate), and the solvent removed in vacuo. The residue is chromatographed (silica gel, 2% methanol/98% dichloromethane) to give the title compound containing 0.10 mol of water; mp 76.5°-77.0° C.

Following the procedure of Example 1, the following compounds are prepared:

EXAMPLE 2

1-(4-Fluorophenyl)-4-[4-(3-pyridinyl)-3-butynyl]-piperazine; mp 97.0°-97.2° C.

EXAMPLE 3

1-(2-Pyridinyl)-4-[4-(3-pyridinyl)-3-butynyl]-piperazine, containing 0.3 mol of water; mp 105.5°-106.2° C.

EXAMPLE 4

2-[4-[4-(3-Pyridinyl)-3-butynyl]-1-piperazinyl]-pyrimidine, containing 0.4 mol of water; mp 96°-97° C.

EXAMPLE 5

1-[4-(5-Nitro-2-pyridinyl)-3-butynyl]-4-(2-pyridinyl)-piperazine

Step (a): Preparation of 4-[(2-pyridyl)-1-piperazinyl]-1-butyne

A solution of 3-butynyl tosylate (25.0 g, 0.11 mol), 1-(2-pyridinyl)piperazine (12.1 g, 0.074 mol), and sodium bicarbonate (6.9 g, 0.082 mol) in 200 mL of dimethylformamide is heated at 80° C. for 18 hours. The solvent is removed under reduced pressure, and the residue is partitioned between 200 mL of dichloromethane and 200 mL of water. The aqueous layer is extracted with 100 mL of dichloromethane and the combined organic layers are dried (sodium sulfate), and the solvent is removed in vacuo. The residue is chromatographed (silica gel, 25% ethyl acetate/75% hexane) to give the title compound as a white solid; mp 57°-58° C.

(step (b): Preparation of 1-[4-(5-Nitro-2-pyridinyl)-3-butynyl]-4-(2-pyridinyl)-piperazine A solution of 2-bromo-5-nitropyridine (3.11 g, 0.015 mol) and the alkyne prepared in Step (a) (3.0 g, 0.014 mol) in 5.8 mL of triethylamine and 60 mL of acetonitrile is degassed by bubbling in dry nitrogen for 15 minutes, and 0.2 g (0.0003 mol) of bis(triphenylphosphine)palladium chloride and 0.05 g (0.0003 mol) of cuprous iodide are added. The flask is flushed with nitrogen and the mixture is stirred at room temperature for 5 hours. The solvent is removed under reduced pressure, and the residue is partitioned between 50 mL of dichloromethane and 50 mL of saturated aqueous sodium bicarbonate. The aqueous layer is extracted with 30 mL of dichloromethane and the combined organic layers are washed with water and dried (sodium sulfate), and the solvent is removed in vacuo. The residue is chromatographed (silica gel, 1% methanol/ 99% dichloromethane) to give the title compound as a brown solid; mp 126°-126.5° C.

Following the procedure of Example 5, the following compound is prepared:

EXAMPLE 6

1-4-(4-Nitrophenyl)-3-butynyl]-4-(2-pyridinyl)piperazine; mp 150°-151° C.

EXAMPLE 7

6-4-[4-(2-Pyridinyl)-1-piperazinyl]-1-butynyl]-3-pyridinamine

A solution of 1-[4-(5-nitro-2-pyridinyl)-3-butynyl]-4-(2-pyridinyl)piperazine (Example 5) (3.5 g, 0.01 mol), reduced iron (4.0 g), and concentrated hydrochloric acid (0.20 mL) in 60 mL of 90% ethanol and 10 mL of water is heated at 80° C. with vigorous stirring for 30 minutes. The hot solution is filtered through diatomaceous earth (Celite) and the filter cake is washed with 500 mL of hot ethanol. The solvent is removed under reduced pressure, and the residue is partitioned between 50 mL of dichloromethane and 50 mL of water. The aqueous layer is washed with 50 mL of dichloromethane and the combined organic layers are dried (sodium sulfate), and the solvent is removed in vacuo. The residue is chromatographed (silica gel, 2% methanol/98% dichloromethane) to give the title compound as a tan solid; mp 140°-141.5° C.

Following the procedure of Example 7, the following compound is prepared:

EXAMPLE 8

4-[4-[4-(2-Pyridinyl)-1-piperazinyl]-benzenamine; mp 119°-120.3° C.

We claim:

1. A compound of Formula I

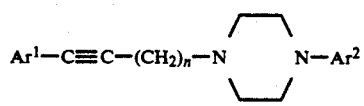

wherein
n is an integer of 2, 3, or 4;
Ar$^1$ and Ar$^2$ are each independently aryl,
aryl substituted by one to four substituents selected from the group consisting of
halogen,
lower alkyl,
lower alkoxy,
lower thioalkoxy,
hydroxy,
lower acyloxy,
amino,
lower alkyl amino
nitro, or

wherein R is
aryl,
lower alkyl,
trifluoromethyl,
2-, 3-, or 4-pyridinyl,
2-, 4-, or 5-pyrimidinyl,
2-pyrazinyl,
2- or 3-furanyl,
2- or 3-thienyl,
2-, 4-, or 5-imidazolyl, or
2-, 4- or 5-thiazolyl,
2-, 3-, or 4-pyridinyl,
2-, 3-, or 4-pyridinyl substituted by
halogen,
lower alkyl,
lower alkoxy,
hydroxy,
lower acyloxy,
amino,
lower alkyl amino,
nitro,

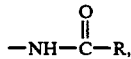

wherein R is as defined above,
—NH—SO$_2$R, wherein R is as defined above, or
—N—(SO$_2$R)$_2$ where R is as defined above,
2-, 4-, or 5-pyrimidinyl,
2-, 4-, or 5-pyrimidinyl substituted by
halogen,
lower alkyl,
lower alkoxy,
hydroxy,
lower acyloxy,
amino,
lower alkyl amino,
nitro,

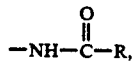

wherein R is as defined above,
—NH—SO₂R, wherein R is as defined above, or
—N—(SO₂R)₂ wherein R is as defined above,
2-pyrazinyl,
2-pyrazinyl substituted by
  halogen,
  lower alkyl,
  lower alkoxy,
  hydroxy,
  lower acyloxy,
  amino,
  lower alkyl amino,
  nitro,

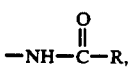

wherein R is as defined above,
—NH—SO₂R, wherein R is as defined above, or
—N—(SO₂R)₂ wherein R is as defined above,
2- or 3-furanyl,
2- or 3-furanyl substituted by
  halogen
  lower alkyl,
  lower alkoxy,
  hydroxy,
  lower acyloxy,
  amino,
  lower alkyl amino,
  nitro,

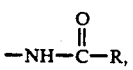

wherein R is as defined above,
—NH—SO₂R, wherein R is as defined above, or
—N—(SO₂R)₂ wherein R is as defined above,
2- or 3-thienyl,
2- or 3-thienyl substituted by
  halogen,
  lower alkyl,
  lower alkoxy,
  hydroxy,
  lower acyloxy,
  amino,
  lower alkyl amino,
  nitro,

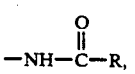

wherein R is as defined above,
—NH—SO₂R wherein R is as defined above, or
—N—(SO₂R)₂ wherein R is as defined above,
2-, 4-, or 5-imidazolyl,
2-, 4-, or 5-imidazolyl substituted by
  halogen,
  lower alkyl,
  lower alkoxy,
  hydroxy,
  lower acyloxy,
  amino,
  lower alkyl amino,
  nitro,

wherein R is as defined above,
—NH—SO₂R, wherein R is as defined above, or
—N—(SO₂R)₂ wherein R is as defined above,
2-, 4-, or 5-thiazolyl,
2-, 4-, or 5-thiazolyl substituted by
  halogen,
  lower alkyl,
  lower alkoxy,
  hydroxy,
  lower acyloxy,
  amino,
  lower alkyl amino,
  nitro,

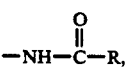

wherein R is as defined above,
—NH—SO₂R wherein R is as defined above, or
—N—(SO₂R)₂ wherein R is as defined above,
2-, 3-, 4-, 5-, 6-, or 7-indolyl,
2-, 3-, 4-, 5-, 6-, or 7-indolyl substituted by
  halogen,
  lower alkyl,
  lower alkoxy,
  hydroxy,
  lower acyloxy,
  amino,
  lower alkyl amino,
  nitro,

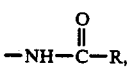

wherein R is as defined above,
—NH—SO₂R, wherein R is as defined above, or
—N—(SO₂R)₂ wherein R is as defined above,
2-, 3-, 4-, 5-, 6-, or 7-benzo[b]thienyl,
2-, 3-, 4-, 5-, 6-, or 7-benzo[b]thienyl substituted by
  halogen,
  lower alkyl,
  lower alkoxy,
  hydroxy,
  lower acyloxy,
  amino,
  lower alkyl amino,
  nitro,

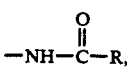

wherein R is as defined above,
—NH—SO₂R, wherein R is as defined above, or
—N—(SO₂R)₂ wherein R is as defined above,
2-, 3-, 4-, 5-, 6-, 7-, or 8-quinolinyl,
2-, 3-, 4-, 5-, 6-, 7-, or 8-quinolinyl substituted by
  halogen,
  lower alkyl, lower alkoxy,
hydroxy,
lower acyloxy,
amino,
lower alkyl amino,
nitro,

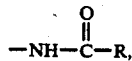

wherein R is as defined above,
—NH—SO$_2$R, wherein R is as defined above, or
—N—(SO$_2$R)$_2$ wherein R is as defined above,
1-, 3-, 4-, 5-, 6-, 7-, or 8-isoquinolinyl,
1-, 3-, 4-, 5-, 6-, 7-, or 8-isoquinolinyl substituted by
halogen,
lower alkyl,
lower alkoxy,
hydroxy,
lower acyloxy,
amino,
lower alkyl amino,
nitro,

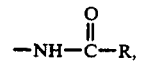

wherein R is as defined above,
—NH—SO$_2$R, wherein R is as defined above, or
—N—(SO$_2$R)$_2$ wherein R is as defined above,
2-, 3-, 4-, 5-, 6-, or 7-(1,8)naphthyridinyl, or
2-, 3-, 4-, 5-, 6-, or 7-(1,8)naphthyridinyl substituted by
halogen,
lower alkyl,
lower alkoxy,
hydroxy,
lower acyloxy,
amino,
lower alkyl amino,
nitro,

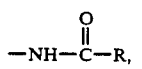

wherein R is as defined above,
—NH—SO$_2$R, wherein R is as defined above, or
—N—(SO$_2$R)$_2$ wherein R is as defined above; or
a pharmaceutically acceptable acid addition salt thereof with the exclusion of a compound wherein
Ar$^1$ and Ar$^2$ are both
aryl,
aryl substituted by one to four substituents selected from the group consisting of
halogen,
lower alkyl,
lower alkoxy,
lower thioalkoxy,
hydroxy,
lower acyloxy,
amino,
lower alkyl amino
nitro, or

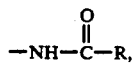

wherein R is
aryl,
lower alkyl,
trifluoromethyl,
2-, 3-, or 4-pyridinyl,
2-, 4-, or 5-pyrimidinyl,
2-pyrazinyl,
2- or 3-furanyl,
2- or 3-thienyl,
2-, 4-, or 5-imidazolyl, or
2-, 4-, or 5-thiazolyl.

2. A compound according to claim 1 in which
n is 2 or 3 and
Ar$^1$ and Ar$^2$ are each independently
aryl,
aryl substituted by one to four substituents selected from the group consisting of
halogen,
lower alkyl,
lower alkoxy,
lower thioalkoxy,
hydroxy,
lower acyloxy,
amino,
lower alkyl amino,
nitro, or

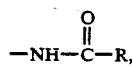

wherein R is
aryl,
lower alkyl,
trifluoromethyl,
2-, 3-, or 4-pyridinyl,
2-, 4-, or 5-pyrimidinyl,
2-pyrazinyl,
2- or 3-furanyl,
2- or 3-thienyl,
2-, 4-, or 5-imidazolyl, or
2-, 4-, or 5-thiazolyl,
2-, 3-, or 4-pyridinyl,
2-, 3-, or 4-pyridinyl substituted by
halogen,
lower alkyl,
lower alkoxy,
hydroxy,
lower acyloxy,
amino,
lower alkyl amino,
nitro,

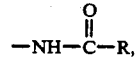

wherein R is as defined above,
—NH—SO$_2$—R, wherein R is as defined above, or
—N—(SO$_2$R)$_2$, wherein R is as defined above,
2-, 4-, or 5-pyrimidinyl,
2-, 4-, or 5-pyrimidinyl substituted by
halogen, lower alkyl,
lower alkoxy,
hydroxy,
lower acyloxy,
amino,
lower alkyl amino,
nitro,

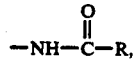

wherein R is as defined above,
—NH—SO₂—R, wherein R is as defined above, or
—N—(SO₂R)₂, wherein R is as defined above,
2- or 3-thienyl,
2- or 3-thienyl substituted by
halogen,
lower alkyl,
lower alkoxy,
hydroxy,
lower acyloxy,
amino,
lower alkyl amino,
nitro,

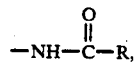

wherein R is as defined above,
—NH—SO₂—R, wherein R is as defined above,
or
—N—(SO₂R)₂, wherein R is as defined above,
4- or 5-thiazolyl,
4- or 5-thiazolyl substituted by
halogen,
lower alkyl,
lower alkoxy,
hydroxy,
lower acyloxy,
amino,
lower alkyl amino,
nitro,

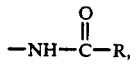

wherein R is as defined above,
—NH—SO₂-R, wherein R is as defined above,
or
—N—(SO₂R)₂, wherein R is as defined above,
2- or 3-indolyl,
2- or 3-indolyl substituted by
halogen,
lower alkyl,
lower alkoxy,
hydroxy,
lower acyloxy,
amino,
lower alkyl amino,
nitro,

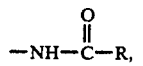

wherein R is as defined above,
—NH—SO₂R, wherein is as defined above, or
—N—(SO₂R)₂ wherein R is as defined above,
2-, 3-, or 4-quinolinyl,
2-, 3-, or 4-quinolinyl substituted by
halogen,
lower alkyl,
lower alkoxy,
hydroxy,
lower acyloxy,
amino,
lower alkyl amino,
nitro,

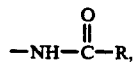

wherein R is as defined above,
—NH—SO₂—R, wherein R is as defined above,
or
—N—(SO₂R)₂, wherein R is as defined above
1-, 3-, or 4-isoquinolinyl, or
1-, 3-, or 4-isoquinolinyl substituted by
halogen,
lower alkyl,
lower alkoxy,
hydroxy,
lower acyloxy,
amino,
lower alkyl amino,
nitro,

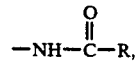

wherein R is as defined above,
—NH—SO₂—R, wherein is as defined above, or
—N—(SO₂R)₂, wherein R is as defined above
with the exclusion of a compound wherein
Ar¹ and Ar² are both
aryl,
aryl substituted by one to four substituents selected
from the group consisting of
halogen,
lower alkyl,
lower alkoxy,
lower thioalkoxy,
hydroxy,
lower acyloxy,
amino,
lower alkyl, amino,
nitro, or

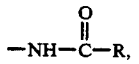

wherein R is
aryl,
lower alkyl,
trifluoromethyl,
2-, 3-, or 4-pyridinyl
2-, 4-, or 5-pyrimidinyl,
2-pyrazinyl
2- or 3-furanyl
2- or 3-thienyl
2-, 4-, or 5-imidazolyl, or 2-, 4-, or 5-thiazolyl.

3. A compound according to claim 2 selected from the group consisting of:

3-[4-[4-(2-Pyridinyl)-1-piperazinyl]-1-butynyl]quinoline;

1-(4-Fluorophenyl)-4-[4-(3-pyridinyl)-3-butynyl]piperazine;

1-(2-Pyridinyl)-4-[4-(3-pyridinyl)-3-butynyl]piperazine;

2-[4-[4-(3-Pyridinyl)-3-butynyl]-1-piperazinyl]pyrimidine;

1-[4-(5-Nitro-2-pyridinyl)-3-butynyl]-4-(2-pyridinyl)piperazine;

1-[4-(4-Nitrophenyl)-3-butynyl]-4-(2-pyridinyl)piperazine;

6-[4-[4-(2-Pyridinyl)-1-piperazinyl]-1-butynyl]-3-pyridinamine;

4-[4-[4-(2-Pyridinyl)-1-piperazinyl]-1-butynyl]benzenamine.

5-[4-[4-(2-Pyridinyl)-1-piperazinyl]-1-butynyl]-2-thiazolamine;

5-[4-[4-(2-Pyridinyl)-1-piperazinyl]-1-butynyl]-2-pyridinamine; and

3-[4-[4-(2-Pyridinyl)-1-piperazinyl]-1-butynyl]-2H-indole;

4. A method of treating schizophrenia comprising administering to a host suffering therefor, a therapeutic effective amount of a compound according to claim 1 in unit dosage form.

5. A pharmaceutical composition adapted for administration as an agent for treating schizophrenia comprising a therapeutic effective amount of compound according to claim 1 in admixture with a pharmaceutically acceptable excipient, diluent, or carrier.

* * * * *

UNITED STATES PATENT AND TRADEMARK OFFICE
CERTIFICATE OF CORRECTION

PATENT NO. : 5,270,312
DATED : December 14, 1993
INVENTOR(S) : Glase et al.

It is certified that error appears in the above-indentified patent and that said Letters Patent is hereby corrected as shown below:

Column 30, line 7, delete "2H" and insert instead "1H".

Column 30, line 10, delete "therefor," and insert instead "therefrom,".

Signed and Sealed this

Twelfth Day of July, 1994

Attest:

BRUCE LEHMAN

Attesting Officer     Commissioner of Patents and Trademarks